United States Patent [19]
Yamamoto et al.

[11] Patent Number: 6,077,670
[45] Date of Patent: Jun. 20, 2000

[54] FLUORESCENT MATERIAL LABELED-PROBE AND METHOD FOR DETECTING HYBRIDIZATION

[75] Inventors: Kenji Yamamoto; Hisanori Nasu; Hitoshi Fujimiya; Noriko Yurino, all of Kanagawa, Japan

[73] Assignee: Hitachi Software Engineering Co., Ltd., Kanagawa, Jordan

[21] Appl. No.: 09/039,278

[22] Filed: Mar. 12, 1998

[30] Foreign Application Priority Data

Sep. 18, 1997 [JP] Japan .................................. 9-253463

[51] Int. Cl.[7] ...................................................... C12Q 1/68
[52] U.S. Cl. ................................................ 435/6; 436/501
[58] Field of Search ...................... 435/6, 91.1; 436/501; 536/25.3

[56] References Cited

U.S. PATENT DOCUMENTS

| | | | |
|---|---|---|---|
| 4,996,143 | 2/1991 | Heller et al. ................................. | 435/6 |
| 5,688,648 | 11/1997 | Mathies et al. ............................. | 435/6 |
| 5,849,489 | 12/1998 | Heller ......................................... | 435/6 |

OTHER PUBLICATIONS

Matthews et al., Analytical Biochemistry, vol. 169, pp. 1–25, 1988.

*Primary Examiner*—Ardin H. Marschel
*Attorney, Agent, or Firm*—Fish & Richardson P.C.

[57] ABSTRACT

A method is disclosed which is capable of increasing a S/N ratio without subjecting a sample to any treatment to thereby detect hybridization with high sensitivity. A fragmentarily divided probe is used which is prepared by dividing a single probe 12 into a plurality of fragmentary probes 12a, 12b, and labeling the fragmentary probes with different fluorescent materials 14a, 14b, respectively. When the probe is hybridized with a sample 11, the fragmentary probes 12a,12b reconstitute the single probe. An intermittent light beam is used as excitation light 19. The fluorescent material 14a is excited therewith, and fluorescence 18 emitted from the fluorescent material 14b through multistep excitation is detected while irradiation with the excitation light is intermitted.

11 Claims, 4 Drawing Sheets

Fig.1(c) combined

Fig.1(d) uncombined

FLUORESCENT MATERIAL LABELED-PROBE AND METHOD FOR DETECTING HYBRIDIZATION

BACKGROUND OF THE INVENTION

1. Field of the Invention

The present invention relates to a method for detecting hybridization which utilizes hybridization between a sample DNA and a probe DNA to analyze whether a DNA sequence of interest is present in the sample DNA or not.

2. Description of the Prior Art

Heretofore, to identify and/or fractionate a molecule found in a living body, in particular, to detect a DNA of interest or to detect presence or absence of a gene DNA, many methods have been employed in which a nucleic acid or protein having a known sequence is hybridized as a probe. In many cases, however, samples used in biochemical experiments are very small in quantity. Accordingly, in analyses thereof, very high sensitivity of detection is required. To cope with this, a probe has been labeled with a radioisotope and hybridized with a sample, and then an X-ray film or the like has been exposed to radiation therefrom to detect the hybridization, thereby performing identification of the sample.

However, a radioisotope is hazardous, and thus handling thereof must be strictly regulated. Accordingly, in recent years, highly sensitive detection methods have been developed which use fluorescence or chemiluminescence instead of a radioisotope. In particular, fluorescent methods have been utilized frequently to detect a sample on a plane because an emission pattern on a plane is recognized as an image by fluorescent methods more easily as compared with chemiluminescence methods. In fluorescent methods, a sample labeled with a fluorescent material is irradiated with a laser beam to excite the fluorescent material, and intensity distribution of fluorescence emitted from the fluorescent material is measured to thereby identify the sample. An example of a device for recognizing such an emission pattern is described in Japanese Examined Patent Publication No.3481/1996.

Figure 2A:
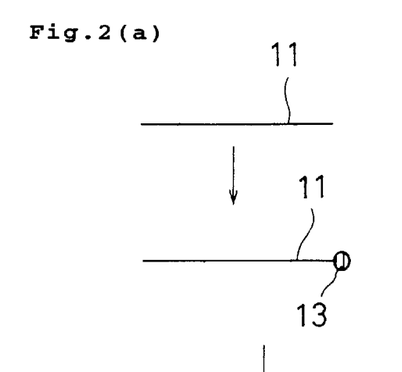
FIGS. 2(a) to 2(f) are a schematic representation illustrating the conventional multi-step excitation method in which a sample and a probe are labeled with fluorescent materials.
Figure 2B:
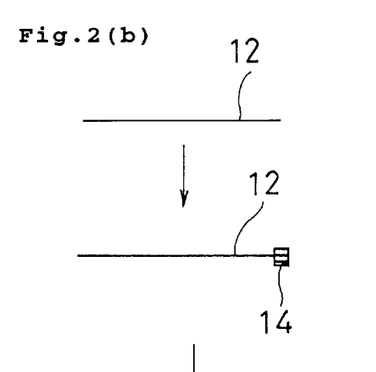

Further, methods have been known which comprises labeling a sample and a probe with different fluorescent materials, and performing hybridization therebetween, followed by detection of the hybridization through multi-step excitation. FIGS. 2(a) to 2(f) are a schematic representation illustrating principle of those methods. As shown in FIG. 2(a), a sample DNA 11 is labeled with a fluorescent material 13, and as shown in FIG. 2(b), a probe DNA 12 is labeled with a fluorescent material 14. The fluorescent material 13 and the fluorescent material 14 are different from each other in excitation wavelength and in fluorescence wavelength. The sample DNA 11 and the probe DNA 12 which have been labeled with the fluorescent materials 13 and 14, respectively, are mixed in a hybridization solution 15. The hybridization solution comprises formaldehyde, SSC (standard saline citrate: NaCl, trisodium citrate), SDS (sodium dodecyl sulfate), EDTA (ethylenediaminetetraacetic acid), and distilled water. Proportions of the ingredients vary depending upon nature of a DNA used.

Figures 2C, 2E:
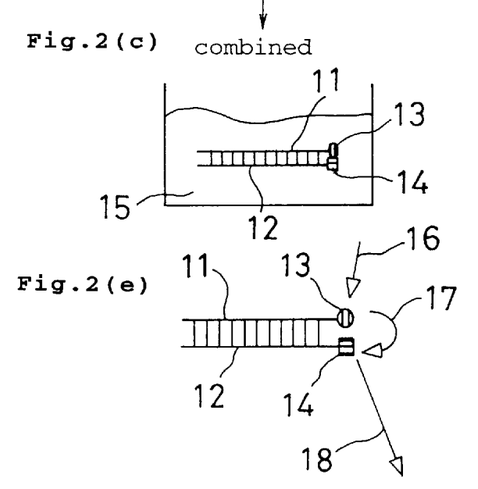
Figures 2D, 2F:
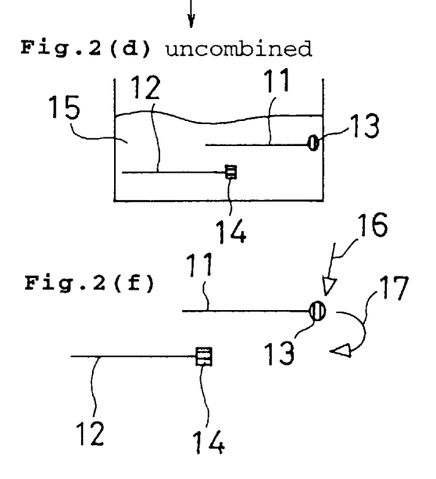

If the sample DNA 11 and the probe DNA 12 are those having complementary strands, they are hybridized into a double-stranded structure as shown in FIG. 2(c). On the other hand, if the sample DNA 11 and the probe DNA 12 are those having uncomplementary strands, they remain uncombined as shown in FIG. 2(d). To detect hybridization between the sample DNA 11 and the probe DNA 12, i.e., to detect whether these DNAs are combined or not, these are irradiated with excitation light 16 from a continuous light source which has a wavelength that allows the fluorescent material 13 to emit light but does not allow the fluorescent material 14 to emit light. If the sample DNA 11 and the probe DNA 12 are hybridized, the fluorescent material 14 is present in the vicinity of the fluorescent material 13, and consequently, excitation energy 17 of the fluorescent material 13 is transferred to the fluorescent material 14, and fluorescence 18 is emitted from the fluorescent material 14, as shown in FIG. 2(e). On the other hand, if the sample DNA 11 and the probe DNA 12 are not hybridized, the fluorescent material 13 with which the sample DNA 11 is labeled and the fluorescent material 14 with which the probe DNA 12 is labeled are distant from each other. Consequently, energy of the fluorescent material 13 cannot be transferred to the fluorescent material 14, and no fluorescence is emitted from the fluorescent material 14, as shown in FIG. 2(f). By observing the wavelength of the fluorescence emitted from the analyte in this manner, it is possible to detect the hybridization between the sample DNA 11 and the probe DNA 12.

Although a fluorescent probe is easy to handle, fluorescence emitted from a fluorescent labeling material is faint and thus its intensity is low. Further, the fluorescence has a wavelength which is not so different from that of excitation light. Accordingly, the excitation light cannot be cut off completely even if an excitation light cut-off filter is disposed in front of a detector. Therefore, highly sensitive detection has not been attained.

When such a probe for multi-step excitation is used, it is possible to increase difference between a wavelength of excitation light and that of fluorescence. This is advantageous in that detection is conducted with the fluorescence apart from the excitation light in wavelength. However, a sample DNA itself must be labeled with a fluorescent material. In a case where a sample DNA is subjected to an artificial treatment such as labeling with a fluorescent material, if an error is made in the step of the artificial treatment, the analysis no longer has reliability at all. If the sample is of vital importance, the error is irretrievable. Further, when the fluorescence is measured, the excitation light partially enters a detector as well together with the fluorescence. Accordingly, it is difficult to increase a S/N ratio.

SUMMARY OF THE INVENTION

The present invention has been made in view of the problems inherent in the conventional techniques. It is, therefore, an object of the present invention to provide a method capable of attaining an improved S/N ratio without subjecting a sample to any treatment to detect hybridization with high sensitivity, and a probe suitable for the detection method.

To attain the above object, the present invention utilizes the fact that a fluorescence having intensity higher than those in the conventional techniques by dividing a single probe into a plurality of fragments, applying different fluorescent materials thereto, respectively, and multi-step-exciting these fluorescent materials. Further, irradiation is performed with intermittent light as excitation light, and fluorescence detection is conducted while a sample is not irradiated with the excitation light, thereby increasing a S/N ratio.

In other words, a fluorescent material-labeled probe according to the present invention comprises:

a plurality of fragmentary probes capable of being hybridized to a plurality of consecutive sites of a DNA, respectively, each of the fragmentary probes being fluorescent material-labeled in such a manner that the fragmentary probes are labeled with different fluorescent materials at positions adjacent to each other when the fragmentary probes are hybridized to the consecutive sites of the DNA.

Further, a fluorescent material-labeled probe according to the present invention comprises:

a plurality of fragmentary probes into which a probe capable of being hybridized with a specific site of a DNA is divided, said probe being labeled with different fluorescent materials at positions in said fragmentary probes, said positions being adjacent to each other when said probe is hybridized to said specific site of the DNA. When a single probe capable of being hybridized to a specific site of a DNA is divided into a plurality of fragmentary probes, it is preferred to cleave the single probe about the middle thereof.

As the fluorescent materials with which the fragmentary probes are labeled, such fluorescent materials are selected that excitation of a fluorescent material with which one of said fragmentary probes is labeled allows the rest of fluorescent materials with which the other fragmentary probes are labeled to emit fluorescence through multi-step excitation.

A method for detecting hybridization according to the present invention comprises:

multi-step-exciting a plurality of labeling fluorescent materials contained in a complex resulting from hybridization of a probe to a specific site of a DNA with a intermittent light beam, and detecting fluorescence resulting from the multi-step excitation while the irradiation with the light is intermitted.

Further, a method for detecting hybridization according to the present invention comprises:

preparing a plurality of fluorescent material-labeled probes capable of being hybridized respectively to a plurality of consecutive sites of a DNA, and exciting a fluorescent material with which one of said probes hybridized with a sample DNA to cause the other probe hybridized with the sample DNA adjacently thereto to emit fluorescence, and detecting the fluorescence resulting from the multi-step excitation.

Still further, a method for detecting hybridization according to the present invention comprises:

dividing a single probe into a plurality of fragmentary probes, labeling said fragmentary probes with different fluorescent materials, hybridizing said fragmentarily divided probe with a sample DNA to thereby reconstitute said single probe composed of said fragmentary probes, exciting a fluorescent material with which one of said fragmentary probes is labeled to cause the other fragmentary probes to emit fluorescence, and detecting the fluorescence resulting from the multi-step excitation.

It is preferred in terms of improvement in S/N ratio that an intermittent light beam be used as fluorescent material excitation light, and fluorescence detection be performed while the irradiation with the light is intermitted.

According to the present invention, by labeling only a probe DNA which can automatically be prepared by an appliance with fluorescent materials, hybridization can be detected by means of fluorescence resulting from multi-step excitation without subjecting an analyte such as a sample DNA to any treatment. By virtue of this, human errors can substantially be prevented from taking place. Further, fluorescent materials may be applied only to a probe DNA, and it is thus possible to prepare fluorescent material-labeled probes in advance as reagent kits. Accordingly, preparatory treatment time for detection of hybridization can be shortened.

Moreover, an intermittent light source is used for multi-step excitation of fluorescent materials, and fluorescence is detected while a sample is not irradiated with excitation light. It is thereby possible to detect the fluorescence without undesired influence of the excitation light having considerably higher intensity as compared with that of the fluorescence. Accordingly, a S/N ratio in the fluorescence detection can be improved, thereby leading to increased sensitivity of hybridization detection.

If it is intended to leave a probe DNA untreated, a sample DNA is divided and labeled with fluorescent materials. In other words, relationship between a sample DNA and a probe DNA may be reversed in the treatment.

BRIEF DESCRIPTION OF THE INVENTION

DESCRIPTION OF THE PREFERRED EMBODIMENTS

In the following, embodiments of the present invention will be described.

Figure 1A:
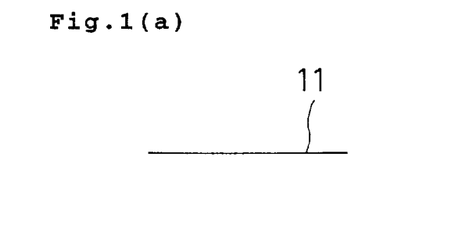
FIGS. 1(a) to 1(f) are a schematic representation illustrating the principle of the present invention.
Figure 1B:
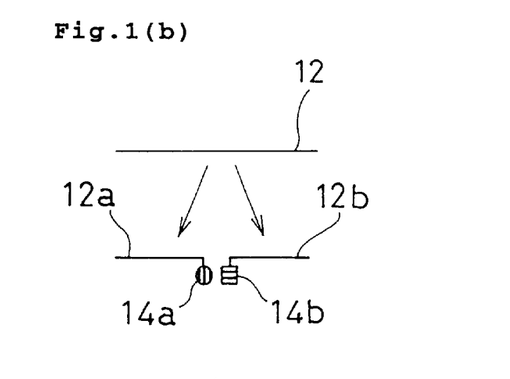

FIGS. 1(a) to 1(f) are a schematic representation illustrating the principle of the present invention. As shown in FIG. 1(a), a sample DNA 11 which is extracted from blood or the like is labeled with no fluorescent materials, and a probe DNA 12 which can be prepared by a synthesizing device is subjected to labeling treatment with fluorescent materials and divided into a plurality of fragments. In other words, as shown in FIG. 1(b), a probe DNA 12 which can be hybridized with a DNA at a specific site is prepared by a synthesizing device and divided into a plurality of fragmentary probe DNAs 12a, 12b. The fragmentary probe DNA 12a is labeled with a fluorescent material 14a, and the fragmentary probe DNA 12b is labeled with a fluorescent material 14b.

The division of the single probe DNA 12 can be performed by cleaving the DNA with a restriction enzyme which cleaves a DNA at a specific position of a sequence. It is preferred to select a position about the middle of the probe DNA as the position of the cleavage. As the fluorescent materials 14a, 14b, those suitable for multi-step excitation are selected according to wavelengths of excitation light. In other words, such a combination thereof is used that when the fluorescent material 14a is photo-excited, the resulting excitation energy is transferred to the other fluorescent material 14b to give rise to light emission from the fluorescent material 14b. For example, when an argon laser beam of 490 nm is used as excitation light, fluoresein isothiocyanate (FITC) is used as the fluorescent material 14a and Texas Red is used as the fluorescent material 14b. The FITC excited with the laser beam of 490 nm emits excitation light of 520 nm. Subsequently, the Texas Red is excited with the excitation light of 520 nm to emit fluorescence of 615 nm.

Positions of labeling with the fluorescent materials 14a, 14b are so selected that when the fragmentary probe DNA 12a and the fragmentary probe DNA 12b are hybridized with a DNA at specific sites of the DNA adjacently to each other, a distance between the fluorescent materials 14a, 14b permits radiation energy of the fluorescent material 14a to excite the fluorescent material 14b. Typically, as the positions of labeling with the fluorescent materials 14a, 14b, those corresponding to the points resulting from the division of the single probe 12 are selected. In view of the fact that a double-stranded DNA has a stereostructure, however, the positions of labeling are not necessarily restricted to those corresponding to the points resulting from the division of the single probe. In short, the positions may be such that when the two fragmentary probes 12a, 12b are hybridized to the specific sites of the sample DNA side by side, the space between the fluorescent material 14a and the fluorescent material 14b permits transfer of energy therebetween.

Figure 1C:
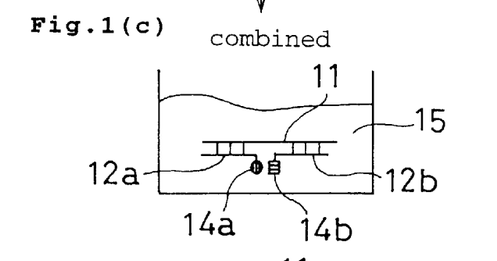
Figure 1D:
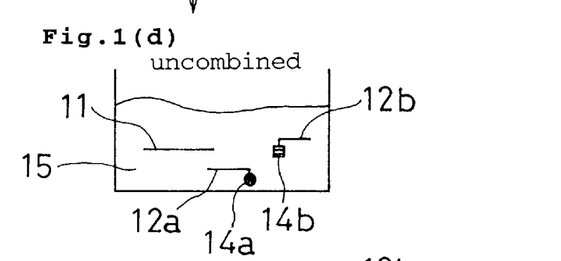

Then, the fragmentary probe DNAs 12a, 12b respectively labeled with the fluorescent materials 14a, 14b are mixed in a hybridization solution 15. The hybridization solution is comprises formaldehyde, SSC (standard saline citrate: NaCl, trisodium citrate), SDS (sodium dodecyl sulfate), EDTA (ethylenediaminetetraacetic acid), and distilled water. Proportions of the ingredients vary depending upon nature of a DNA used. If the sample DNA 11 and the original probe DNA 12 are those having complementary strands, the sample DNA 11 and the fragmentary probe DNAs 12a, 12b are hybridized into a double-stranded structure as shown in FIG. 1(c). On the other hand, if the sample DNA 11 and the probe DNA 12 before the division are those having uncomplementary strands, the sample DNA and the fragmentary probe DNAs 12a, 12b remain uncombined as shown in FIG. 1(d).

To detect hybridization between the sample DNA 11 and the fragmentary probe DNAs 12a, 12b, the analyte is irradiated with excitation light from an excitation light source as intermittent light 19, which has a wavelength that allows the fluorescent material 14a to emit light but does not allow the fluorescent material 14b to emit light. The intermittent excitation light 19 can be generated by using a pulsed laser as the excitation light source or by intermittently interrupting a light beam emitted from a continuous light source by means of light interrupting means such as a shutter.

Figure 1E:
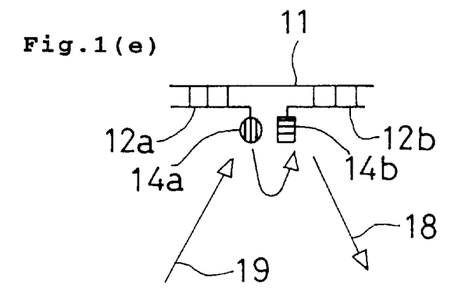
Figure 1F:
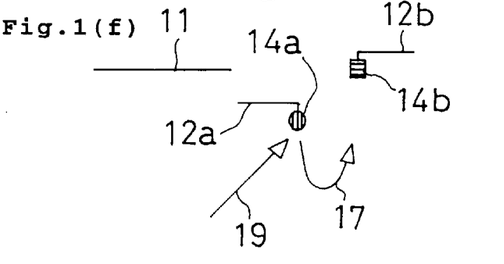

If the sample DNA 11 and the fragmentary probe DNAs 12a, 12b are hybridized, the fluorescent material 14b is present in the vicinity of the fluorescent material 14a, and consequently, excitation energy 17 of the fluorescent material 14a is transferred to the fluorescent material 14b, and fluorescence 18 is emitted from the fluorescent material 14b, as shown in FIG. 1(e). On the other hand, if the sample DNA 11 and the fragmentary probe DNAs 12a, 12b are not hybridized, the fluorescent material 14a with which the fragmentary probe DNA 12a is labeled and the fluorescent material 14b with which the fragmentary probe DNA 12b is labeled are distant from each other. Consequently, energy of the fluorescent material 14a cannot be transferred to the fluorescent material 14b, and no fluorescence is emitted from the fluorescent material 14b, as shown in FIG. 1(f). By observing the wavelength of the fluorescence emitted from the analyte in this manner, it is possible to detect the hybridization between the sample DNA 11 and the fragmentary probe DNAs 12a, 12b which is equivalent to hybridization between the sample DNA 11 and the probe DNA 12.

Figure 3:
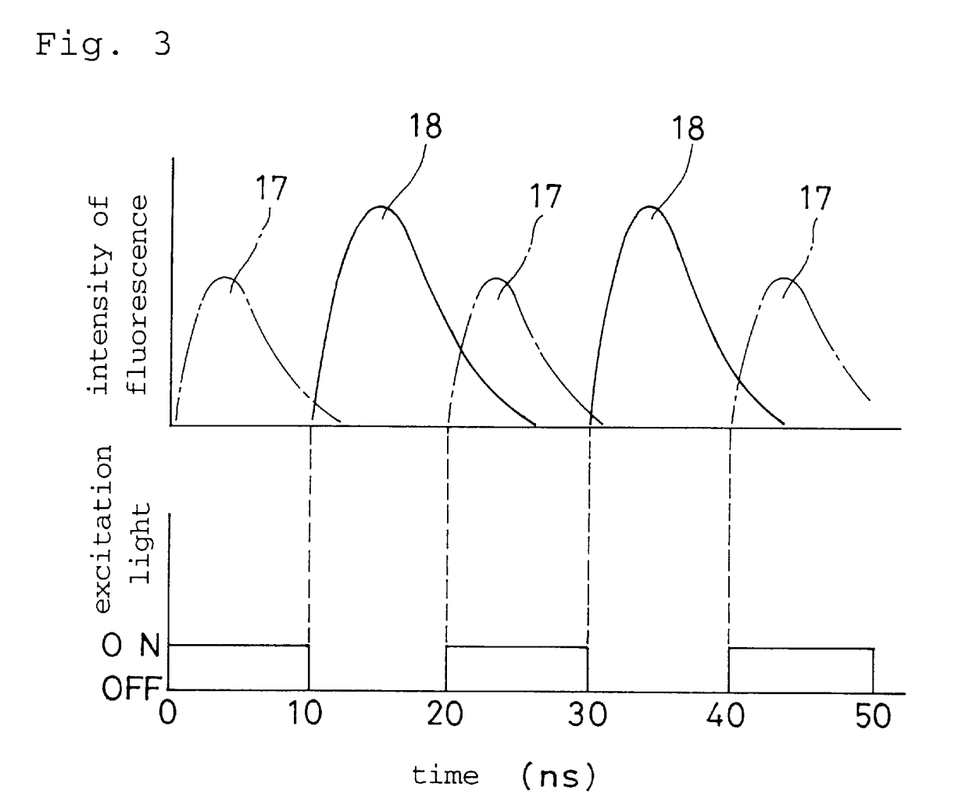
FIG. 3 is a graphical representation illustrating relationship between timing of irradiation with intermittent excitation light and emission of light from fluorescent materials.

FIG. 3 is an explanatory representation of relationship between timing of the irradiation with the intermittent excitation light 19 and the emitted light 17 from the fluorescent material 14a and the emitted light 18 from the fluorescent material 14b in FIGS. 1(e) and 1(f). In FIG. 3, condition where the analyte is irradiated with the intermittent excitation light 19 and condition where the excitation light 19 is interrupted and the analyte is not irradiated therewith are represented as ON and OFF, respectively. Under the condition where the analyte is irradiated with the intermittent excitation light 19, the fluorescent material 14a is excited with the intermittent excitation light 19.

If the sample DNA 11 and the fragmentary probe DNAs 12a, 12b are hybridized as shown in FIG. 1(e), the excitation energy of the fluorescent material 14a is transferred to the fluorescent material 14b. In consequence, the fluorescence 18 is emitted from the fluorescent material 14b through the multi-step excitation. On the other hand, if the sample DNA 11 and the fragmentary probe DNAs 12a, 12b are not hybridized as shown in FIG. 1(f), the energy of the fluorescent material 14a cannot be transferred to the fluorescent material 14b. In consequence, the fluorescence 17 is emitted from the fluorescent material 14a, but the fluorescent material 14b is not excited and thus no fluorescence 18 is emitted therefrom. By virtue of such timing that when the fluorescent 18 derived from the multi-step excitation is emitted, the intermittent excitation light 19 is interrupted, the fluorescence 18 can be detected with high sensitivity at a high S/N ratio without undesired influence of the excitation light 19 having extremely high intensity.

In addition, even in the conventional detection method where a sample DNA and a probe DNA is labeled with different fluorescent materials and hybridization between the sample DNA and the probe DNA is detected through multi-step excitation, if intermittent light is used as the fluorescent material excitation light to detect the fluorescence derived from the multi-step excitation while the excitation light is interrupted, an improved S/N ratio of a detected signal can be attained as compared with excitation with continuous light.

In view of the present situation that selectable wavelengths of oscillation of an excitation laser are restricted, increased efficiency of fluorescent material excitation can be attained by utilizing multi-step excitation as compared with that in a case where a fluorescent probe using one fluorescent material is employed. In other words, a fluorescent material which is efficiently excited with light of a wavelength of an excitation laser is selected as a first fluorescent material, and a fluorescent material which is efficiently excited with a wavelength of the light emitted by the first fluorescent material is selected as a second fluorescent material. By virtue of this, efficiency of fluorescent material excitation as a whole can be increased as compared with that obtained by directly exciting one fluorescent material.

Figure 4A:
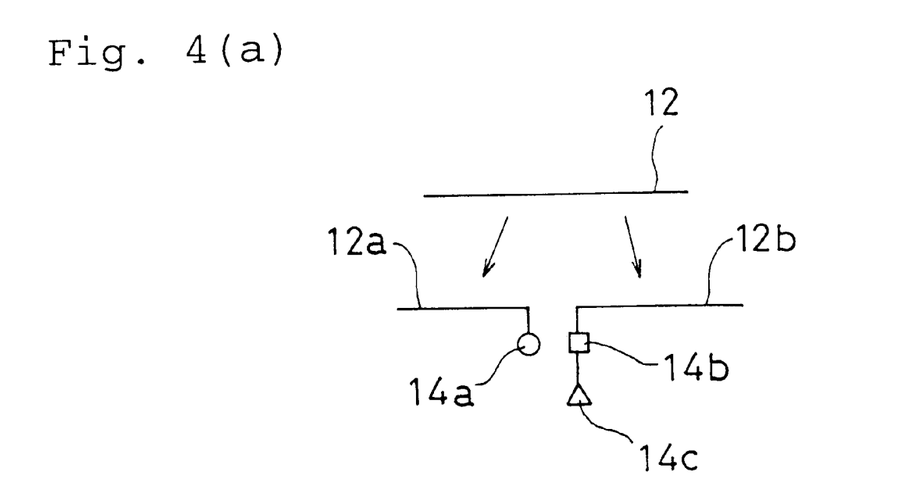
FIGS. 4(a) to 4(b) are an illustrative representation other embodiments of the fluorescent material-labeled probe according to the present invention.
Figure 4B:
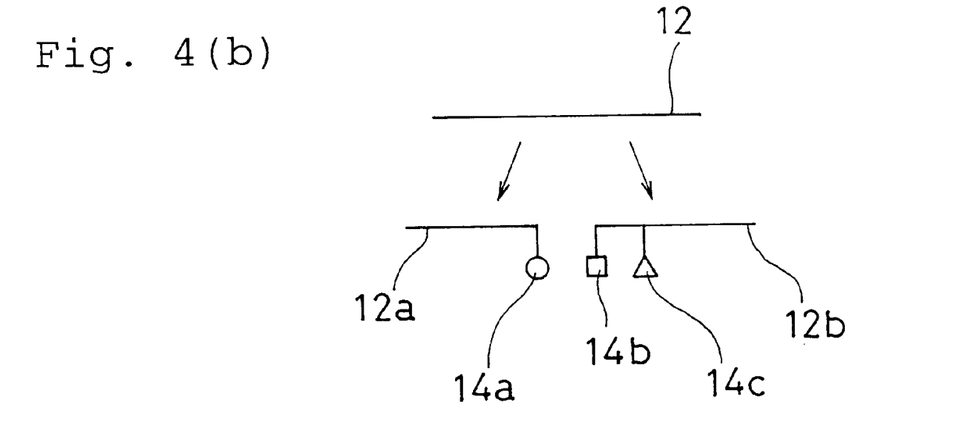

Further, each of fragmentary probe DNAs is not necessarily labeled with one fluorescent material. FIGS. 4(a) to 4(b) are an illustrative representation of other embodiments of the fluorescent material-labeled probes according to the present invention, one of fragmentary probes of which is labeled with a plurality of fluorescent materials. Description will be given on embodiments using three fluorescent materials.

In the embodiment in FIG. 4(a), a probe DNA 12 which can be hybridized with a DNA at a specific site is divided into a plurality of fragmentary probe DNAs 12a, 12b, and the fragmentary probe DNA 12a is labeled with a fluorescent material 14a and the fragmentary probe DNA 12b is labeled with fluorescent materials 14b, 14c. The fluorescent material 14b is connected to the fluorescent material 14c. As excitation light, there is used light which is capable of exciting the fluorescent material 14a but not directly capable of exciting the fluorescent material 14b nor fluorescent material 14c. In this connection, a wavelength of fluorescence of the fluorescent material 14a is capable of exciting the fluorescent material 14b, and a wavelength of fluorescence of the fluorescent material 14b is capable of exciting the fluorescent material 14c, but the wavelength of the fluorescence of the fluorescent material 14a is not capable of exciting the fluorescent material 14c.

As an example of such a combination of the fluorescent materials, there may be mentioned a combination of fluoresein isothiocyanate (FITC) which is excited at a wavelength of 490 nm to emit fluorescence of 520 nm in wavelength, Texas Red which is excited at a wavelength of 580 nm to emit fluorescence of 602 nm in wavelength, and Cy5 which is excited at a wavelength of 650 nm to emit fluorescence of 667 nm in wavelength.

The embodiment in FIG. 4(b) is in common with the embodiment in FIG. 4(a) in that the fragmentary probe DNA 12b is labeled with the fluorescent materials 14b, 14c, but it is different from the embodiment in FIG. 4(a) in that positions of labelings with the fluorescent materials 14b, 14c are both on the fragmentary probe DNA 12b.

In each embodiment in FIG. 4(a) and 4(b) which uses three fluorescent materials, detection of hybridization is performed by observing whether or not fluorescence derived from multi-step excitation is detected from the fluorescent material 14c in consequence of irradiation of the fluorescent material 14a with excitation light capable of exciting the same. In other words, if hybridization between the sample DNA and the fragmentary probe DNAs 12a, 12b has taken place, the fluorescence is detected from the fluorescent material 14c through the multi-step excitation. However, if hybridization between the sample DNA 11 and the fragmentary probe DNAs 12a, 12b has not taken place, only fluorescence from the fluorescent material 14a is detected and no fluorescence from the fluorescent material 14c is detected. By utilizing the multi-step excitation using three fluorescent materials or more in combination as described above, efficiency of fluorescent material excitation of the fluorescent material system as a whole can be increased as in the case of the two-step excitation. Further, it is possible to put the wavelength of the fluorescence resulting from the multi-step excitation considerably apart from that of the excitation light. This is advantageous in that the fluorescence is detected with the excitation light apart therefrom in wavelength.

In the following, a specific application example of the present invention will be described. In this example, description will be given on v-myb (0.52 kb) which is one of DNA probes for onocogene diagnosis.

The v-myb probe has a recognition site for restriction enzyme FokI about 300th bp. Accordingly, when the v-myb probe is cleaved using FokI, two fragments of about 300 bp and of about 200 bp are obtained. Then, 3'-terminal of the fragment of about 300 bp and 5'-terminal of the fragment of about 200 bp are labeled with different fluorescent materials. As a combination of the fluorescent materials, Texas Red and Cy5 are used. Then, into a hybridization solution containing the two fragments, a sample DNA is placed to conduct hybridization in the solution. Then, detection of the hybridization is carried out. In the detection, a semiconductor-excited solid state laser is used as a light source, which emits light of 532 nm and is pulsed by a photoacoustic element. Pulse intervals are selected such that a laser beam is ON for 10 ns and OFF for 20 ns, and quantity of fluorescence from 5 to 15 ns after change to OFF is measured by a photomultiplier tube through an optical interference filter of 675 nm. As a result, the measurement according to the method of the present invention can be carried out with sensitivity about 100 times that of the example of conventional techniques using multi-step excitation.

Herein, the method has been described which comprises reacting a sample DNA with a probe labeled with fluorescent materials in a solution to perform hybridization. It is, however, to be noted that the probe labeled with fluorescent materials according to the present invention may, of course, be applied to a method for detecting blot hybridization in which a probe is blotted on a membrane.

According to the present invention, without subjecting a sample DNA to any treatment, sensitivity of hybridization detection can be increased by utilizing multi-step excitation of fluorescent materials.

What is claimed is:

1. A method for detecting hybridization comprising:

preparing a plurality of fluorescent material-labeled probes capable of being hybridized respectively to a plurality of consecutive sites of a nucleic acid molecule;

hybridizing the probes to the nucleic acid molecule;

intermittently exciting a fluorescent material with which one of said probes is labeled to cause the other probe hybridized with the nucleic acid adjacent thereto to emit fluorescence; and detecting the fluorescence resulting from the multi-step excitation.

2. The method of claim 1, wherein the nucleic acid molecule is DNA or RNA.

3. The method for detecting hybridization of claim 1, wherein the fluorescent material is selected from the group consisting of fluorescein isothiocyanate (FITC), Texas Red, and Cy5.

4. A method for detecting hybridization comprising:

dividing a single probe into a plurality of fragmentary probes;

labeling said fragmentary probes with different fluorescent materials;

hybridizing said fragmentary divided probe with a sample nucleic acid molecule to thereby reconstitute said single probe composed of said fragmentary probes;

intermittently exciting a fluorescent material with which one of said fragmentary probes is labeled to cause the other fragmentary probes to emit fluorescence; and detecting the fluorescence resulting from the multi-step excitation.

5. The method of claim 4, wherein the nucleic acid molecule is DNA or RNA.

6. The method for detecting hybridization of claim 4, wherein the fluorescent material is selected from the group consisting of fluorescein isothiocyanate (FITC), Texas Red, and Cy5.

7. The method for detecting hybridization according to claim 1 or 4, wherein an intermittent light beam is used as florescent material excitation light, and the fluorescence is detected while the irradiation with the light is intermitted.

8. A method for detecting hybridization comprising:

dividing a single probe into a plurality of fragmentary probes;

labeling said fragmentary probes with different fluorescent materials;

hybridizing said fragmentary divided probe with a sample DNA molecule to thereby reconstitute said single probe composed of said fragmentary probes;

intermittently exciting a fluorescent material with which one of said fragmentary probes is labeled to cause the other fragmentary probes to emit fluorescence, and detecting the fluorescence resulting from the multi-step excitation.

9. The method for detecting hybridization of claim 8, wherein an intermittent light beam is used as florescent material excitation light, and the fluorescence is detected while the irradiation with the light is intermitted.

10. The method for detecting hybridization of claim 8, wherein the fluorescent material is selected from the group consisting of fluorescein isothiocyanate (FITC), Texas Red, and Cy5.

11. A method for detecting hybridization comprising:

dividing a single probe into a plurality of fragmentary probes;

labeling said fragmentary probes with different fluorescent materials;

hybridizing said fragmentary divided probe with a sample DNA molecule to thereby reconstitute said single probe composed of said fragmentary probes;

intermittently exciting a fluorescent material with which one of said fragmentary probes is labeled to cause the other fragmentary probes to emit fluorescence wherein the fluorescent material is selected from the group consisting of fluorescein isothiocyanate (FITC), Texas Red and Cy5 and wherein at least one probe is labeled with Cy5, and detecting the fluorescence resulting from the multi-step excitation.

* * * * *

UNITED STATES PATENT AND TRADEMARK OFFICE
CERTIFICATE OF CORRECTION

PATENT NO. : 6,077,670
DATED : June 20, 2000
INVENTOR(S) : Kenji Yamamota, Hisanori Nasu, Hitoshi Fujimiya, and Noriko Yurino It is certified that error appears in the above-identified patent and that said Letters Patent is hereby corrected as shown below:

[22] Filed: Mar. 13, 1998

[73] Assignee: Hitachi Software Engineering Co., Ltd., Kanagawa, Japan

Signed and Sealed this

Twelfth Day of June, 2001

*Attest:*

*Attesting Officer*

NICHOLAS P. GODICI
*Acting Director of the United States Patent and Trademark Office*